(12) United States Patent  (10) Patent No.: US 8,430,809 B2
Cabiri et al.  (45) Date of Patent: Apr. 30, 2013

(54) CAPSULE FOR USE IN SMALL INTESTINE

(75) Inventors: Oz Cabiri, Macabim (IL); Benad Goldwasser, Tel Aviv (IL); Borisr Degtiar, Modi'in (IL)

(73) Assignee: G. I View Ltd., Ramat Gan (IL)

( * ) Notice: Subject to any disclaimer, the term of this patent is extended or adjusted under 35 U.S.C. 154(b) by 1607 days.

(21) Appl. No.: 11/672,369

(22) Filed: Feb. 7, 2007

(65) Prior Publication Data

US 2007/0244359 A1 Oct. 18, 2007

Related U.S. Application Data

(63) Continuation-in-part of application No. PCT/IL2006/000889, filed on Aug. 1, 2006.

(60) Provisional application No. 60/704,654, filed on Aug. 1, 2005, provisional application No. 60/881,036, filed on Jan. 17, 2007.

(51) Int. Cl.
*A61B 1/04* (2006.01)
(52) U.S. Cl.
USPC .......................... 600/116; 600/114; 600/115
(58) Field of Classification Search .......... 600/114–116, 600/153–159; 604/95.05, 95.03, 101.02
See application file for complete search history.

(56) References Cited

U.S. PATENT DOCUMENTS

| 3,895,637 A | 7/1975 | Choy |
| 3,924,625 A | 12/1975 | Peterson |
| 4,040,413 A | 8/1977 | Ohshiro et al. |
| 4,066,070 A | 1/1978 | Utsugi |
| 4,077,610 A | 3/1978 | Masuda et al. |
| 4,530,698 A | 7/1985 | Goldstein et al. |
| 4,561,427 A | 12/1985 | Takada |
| 4,566,763 A | 1/1986 | Greguss et al. |
| 4,596,381 A | 6/1986 | Hamrick |
| 4,690,131 A | 9/1987 | Lyddy, Jr. et al. |
| 4,838,859 A | 6/1989 | Strassmann |
| 4,971,034 A | 11/1990 | Doi et al. |
| 4,976,524 A | 12/1990 | Chiba |
| 5,353,807 A | 10/1994 | DeMarco |
| 5,364,353 A | 11/1994 | Corfitsen et al. |
| 5,395,332 A | 3/1995 | Ressemann et al. |

(Continued)

FOREIGN PATENT DOCUMENTS

| EP | 0242428 | 10/1987 |
| EP | 0267446 | 5/1988 |

(Continued)

*Primary Examiner* — Matthew J Kasztejna
(74) *Attorney, Agent, or Firm* — Frommer Lawrence & Haug LLP; William S. Frommer

(57) ABSTRACT

Apparatus for use in a body lumen is provided including an introducer tube configured to be advanced into a gastrointestinal tract of a subject. A guide member is coupled to a distal end of the introducer tube and is configured to be mounted in a vicinity of a valve of the subject. The apparatus also includes a capsule removably coupled to a distal portion of the introducer tube, and configured to be decoupled from the introducer tube and propelled through a small intestine of the subject once the guide member has been mounted in the vicinity of the valve. The apparatus also includes a gas supply configured to propel the capsule distally through the small intestine by generating positive gas pressure proximal to the capsule. Other embodiments are also described.

46 Claims, 5 Drawing Sheets

U.S. PATENT DOCUMENTS

| | | | |
|---|---|---|---|
| 5,398,670 A | 3/1995 | Ortiz et al. | |
| 5,471,988 A | 12/1995 | Fujio et al. | |
| 5,473,474 A | 12/1995 | Powell et al. | |
| 5,509,371 A | 4/1996 | Phillips | |
| 5,571,114 A | 11/1996 | Devanaboyina | |
| 5,586,968 A | 12/1996 | Grundl et al. | |
| 5,604,531 A | 2/1997 | Iddan et al. | |
| 5,662,587 A | 9/1997 | Grundfest et al. | |
| 5,728,068 A | 3/1998 | Leone et al. | |
| 5,863,284 A | 1/1999 | Klein | |
| 5,879,325 A | 3/1999 | Lindstrom et al. | |
| 5,906,357 A | 5/1999 | Munson, Sr. | |
| 5,906,591 A | 5/1999 | Dario et al. | |
| 5,910,105 A | 6/1999 | Swain et al. | |
| 5,941,815 A | 8/1999 | Chang | |
| 5,984,860 A | 11/1999 | Shan | |
| 6,007,482 A | 12/1999 | Madni et al. | |
| 6,028,719 A | 2/2000 | Beckstead et al. | |
| 6,071,234 A | 6/2000 | Takada | |
| 6,130,783 A | 10/2000 | Yagi et al. | |
| 6,157,018 A | 12/2000 | Ishiguro et al. | |
| 6,240,312 B1 * | 5/2001 | Alfano et al. | 600/476 |
| 6,277,065 B1 | 8/2001 | Donofrio | |
| 6,315,713 B1 | 11/2001 | Takada | |
| 6,332,865 B1 | 12/2001 | Borody et al. | |
| 6,333,826 B1 | 12/2001 | Charles | |
| 6,341,044 B1 | 1/2002 | Driscoll, Jr. et al. | |
| 6,356,296 B1 | 3/2002 | Driscoll, Jr. et al. | |
| 6,373,642 B1 | 4/2002 | Wallerstein et al. | |
| 6,388,820 B1 | 5/2002 | Wallerstein et al. | |
| 6,422,989 B1 | 7/2002 | Hektner | |
| 6,424,377 B1 | 7/2002 | Driscoll, Jr. et al. | |
| 6,439,032 B1 | 8/2002 | Lehmann et al. | |
| 6,440,061 B1 * | 8/2002 | Wenner et al. | 600/114 |
| 6,449,103 B1 | 9/2002 | Charles | |
| 6,459,451 B2 | 10/2002 | Driscoll, Jr. et al. | |
| 6,485,409 B1 | 11/2002 | Voloshin et al. | |
| 6,493,032 B1 | 12/2002 | Wallerstein et al. | |
| 6,503,192 B1 | 1/2003 | Ouchi et al. | |
| 6,517,477 B1 | 2/2003 | Wendlandt | |
| 6,527,705 B1 | 3/2003 | Ouchi | |
| 6,537,206 B2 | 3/2003 | Takada | |
| 6,597,520 B2 | 7/2003 | Wallerstein et al. | |
| 6,599,237 B1 | 7/2003 | Singh | |
| 6,611,282 B1 | 8/2003 | Trubko et al. | |
| 6,646,818 B2 | 11/2003 | Doi | |
| 6,648,814 B2 | 11/2003 | Kim et al. | |
| 6,682,479 B1 | 1/2004 | Takahashi et al. | |
| 6,695,771 B2 | 2/2004 | Takada et al. | |
| 6,702,734 B2 | 3/2004 | Kim et al. | |
| 6,704,148 B2 | 3/2004 | Kumata | |
| 6,709,388 B1 | 3/2004 | Mosse et al. | |
| 6,719,684 B2 | 4/2004 | Kim et al. | |
| 6,743,208 B1 | 6/2004 | Coyle | |
| 6,764,441 B2 | 7/2004 | Chiel et al. | |
| 6,786,864 B2 | 9/2004 | Matsuura et al. | |
| 6,800,056 B2 | 10/2004 | Tartaglia et al. | |
| 6,814,728 B2 | 11/2004 | Ouchi et al. | |
| 6,824,510 B2 | 11/2004 | Kim et al. | |
| 6,827,718 B2 | 12/2004 | Hutchins et al. | |
| 6,837,846 B2 | 1/2005 | Jaffe et al. | |
| 6,866,626 B2 | 3/2005 | Long et al. | |
| 6,869,393 B2 | 3/2005 | Butler et al. | |
| 6,911,005 B2 | 6/2005 | Ouchi et al. | |
| 6,932,323 B2 | 8/2005 | James | |
| 6,958,034 B2 * | 10/2005 | Iddan | 600/114 |
| 6,974,441 B2 | 12/2005 | Ravo et al. | |
| 7,056,283 B2 | 6/2006 | Baror et al. | |
| 2001/0051766 A1 * | 12/2001 | Gazdzinski | 600/309 |
| 2002/0012059 A1 | 1/2002 | Wallerstein et al. | |
| 2002/0072651 A1 | 6/2002 | Vilos | |
| 2002/0109772 A1 | 8/2002 | Kuriyama et al. | |
| 2002/0109773 A1 | 8/2002 | Kuriyama et al. | |
| 2003/0074015 A1 | 4/2003 | Nakao | |
| 2003/0181788 A1 | 9/2003 | Yokoi et al. | |
| 2003/0191369 A1 | 10/2003 | Arai et al. | |
| 2003/0208219 A1 | 11/2003 | Aznoian et al. | |
| 2003/0225433 A1 | 12/2003 | Nakao | |
| 2004/0004836 A1 | 1/2004 | Dubuc | |
| 2004/0111010 A1 | 6/2004 | Nishiie | |
| 2004/0143161 A1 | 7/2004 | Baror et al. | |
| 2004/0199087 A1 | 10/2004 | Swain et al. | |
| 2004/0199088 A1 | 10/2004 | Bakos et al. | |
| 2004/0199196 A1 | 10/2004 | Ravo | |
| 2004/0204702 A1 | 10/2004 | Ziegler et al. | |
| 2004/0249247 A1 | 12/2004 | Iddan | |
| 2004/0260150 A1 | 12/2004 | Bernstein | |
| 2005/0038317 A1 | 2/2005 | Ratnakar | |
| 2005/0038319 A1 | 2/2005 | Goldwasser et al. | |
| 2005/0085841 A1 | 4/2005 | Eversull et al. | |
| 2005/0095200 A1 | 5/2005 | Schwarzberg | |
| 2005/0107664 A1 | 5/2005 | Kalloo et al. | |
| 2005/0154355 A1 | 7/2005 | Gross et al. | |
| 2005/0165272 A1 | 7/2005 | Okada et al. | |
| 2005/0288551 A1 * | 12/2005 | Callister et al. | 600/115 |
| 2006/0164733 A1 | 7/2006 | Gal et al. | |
| 2006/0238879 A1 | 10/2006 | Togino | |
| 2010/0137686 A1 | 6/2010 | Meron et al. | |

FOREIGN PATENT DOCUMENTS

| | | | |
|---|---|---|---|
| EP | 0659387 | | 6/1995 |
| FR | 1465723 | | 3/1967 |
| JP | 1992-144533 | * | 5/1992 |
| JP | 7313443 | | 12/1995 |
| JP | 2002031766 | | 1/2002 |
| JP | 2006026344 | | 2/2006 |
| WO | 00/44275 A1 | | 8/2000 |
| WO | 0168540 | | 9/2001 |
| WO | 02059676 | | 8/2002 |
| WO | 02075348 | | 9/2002 |
| WO | 03026272 | | 3/2003 |
| WO | 03046830 | | 6/2003 |
| WO | 03053225 | | 7/2003 |
| WO | 2004008185 | | 1/2004 |
| WO | 2004/016299 | | 2/2004 |
| WO | 2004010858 | | 2/2004 |
| WO | 2006/025045 | | 3/2006 |

* cited by examiner

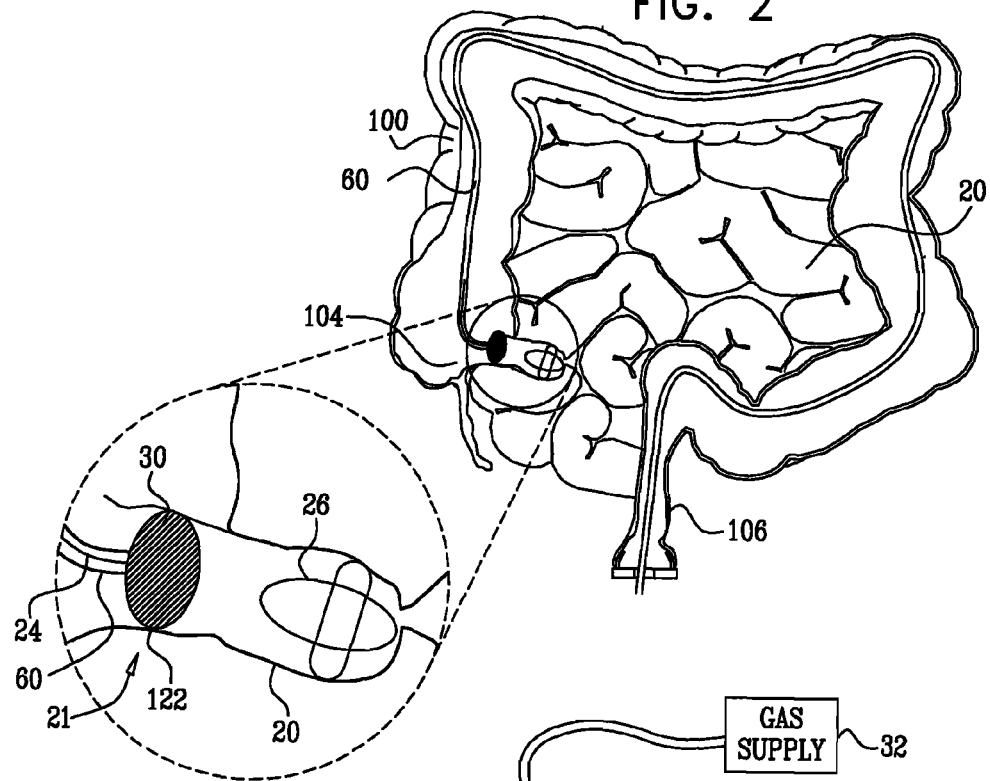
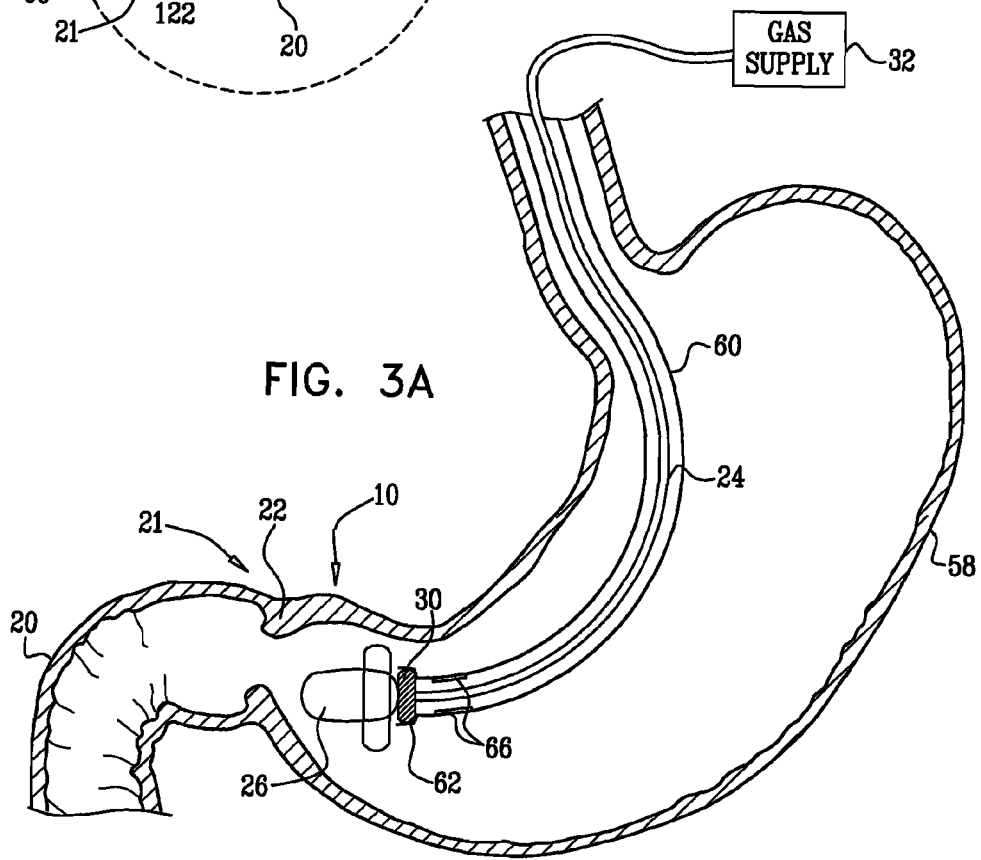

CAPSULE FOR USE IN SMALL INTESTINE

CROSS-REFERENCES TO RELATED APPLICATIONS

The present application:

(a) is a continuation-in-part of PCT Application no. PCT/IL2006/000889, filed Aug. 1, 2006, which claims the benefit of U.S. Provisional Patent Application 60/704,654 to Goldwasser et al., entitled, "Tools for use in small intestine," filed Aug. 1, 2005, and (b) claims the priority of U.S. provisional patent application No. 60/881,036 to Cabiri entitled, "Diagnostic or treatment tool for colonoscopy," filed Jan. 17, 2007.

These applications are assigned to the assignee of the present patent application and are incorporated herein by reference.

FIELD OF THE INVENTION

The present invention relates generally to apparatus for use in a body lumen. Specifically, the present invention relates to a pressure-propelled system, suitable for imaging body lumens, such as the gastrointestinal (GI) tract.

BACKGROUND OF THE INVENTION

Techniques for evaluating the small bowel include CT enterography, ultrasonography, nuclear medicine, and magnetic resonance imaging. Currently, a standard method of detecting abnormalities in the small intestine is through endoscopic examination, in which a doctor advances a scope into the small intestine via the mouth.

U.S. Pat. No. 6,958,034 to Iddan et al., which is incorporated herein by reference, describes a sensing device including a propulsion system that is typically, substantially, or completely within the sensing device. The propulsion system is described to include, for example, a rotatable propeller. The sensing device is described as an in-vivo autonomous capsule with an imager, but may be another type of sensing device.

US Patent Application Publication 2005/0154355 to Gross et al., which is incorporated herein by reference, describes apparatus for use with a fluid gas supply. The apparatus includes an elongate carrier, adapted to be inserted through a proximal opening of a body lumen, and a distal piston head coupled to a distal portion of the carrier. The piston head is adapted to be in direct contact with a wall of the lumen when the carrier is inserted into the lumen, and to be advanced distally through the body lumen in response to pressure from the fluid gas supply.

US Patent Application Publication 2005/0036059 to Goldwasser, which is incorporated herein by reference, describes an ingestible imaging system including an ingestible housing. The housing includes an imaging sensor and a motor-driven propulsion device.

US Patent Application Publication 2005/0038335 to Gross et al., which is incorporated herein by reference, describes a system including a guide member at least partially insertable into a proximal opening of a body lumen, the guide member including a first passageway connectable to a source of fluid pressure, an elongate carrier arranged for sliding movement through the guide member, and a piston head mounted on the carrier, wherein a greater fluid pressure acting on a proximal side of the piston head than on a distal side of the piston head propels the piston head and the carrier in a distal direction in the body lumen.

PCT Publication WO 05/065044 to Cabiri et al., which is incorporated herein by reference, describes apparatus for use with a biologically-compatible-fluid gas supply. The apparatus includes an elongate carrier, adapted to be inserted through a proximal opening of a body lumen, and a piston head coupled to a distal portion of the carrier. The piston head is adapted to form a pressure seal with a wall of the lumen after the carrier has been inserted into the lumen, and to be advanced distally through the body lumen in response to pressure from the fluid gas supply. The apparatus is configured to facilitate distal advancement of the piston head by facilitating passage of fluid out of the lumen from a site within the lumen distal to the piston head.

U.S. Pat. No. 6,709,388 to Mosse et al., which is incorporated herein by reference, describes a self-propelling device adapted to travel through a passage, such as a gut, having walls containing contractile tissue. The device comprises a body and at least one contractile tissue-stimulating means, such as electrodes, for stimulating the walls to urge the device selectively in both a forward direction.

The following patents and patent applications, which are incorporated herein by reference, may be of interest:

U.S. Pat. No. 5,984,860 to Shan et al.
U.S. Pat. No. 6,866,626 to Long et al.
U.S. Pat. No. 6,682,479 to Takahashi et al.
US Patent Application Publication 2005/0095200 to Schwarzberg et al.
U.S. Pat. No. 6,071,234 to Takada et al.
U.S. Pat. No. 5,571,114 to Devanaboyina
US Patent Application Publication 2004/0260150 to Bernstein
US Patent Application Publication 2005/0038317 to Ratnakar.
U.S. Pat. No. 6,869,393 to Butler
U.S. Pat. No. 5,941,815 to Chang
U.S. Pat. No. 5,879,325 to Lindstrom et al.
U.S. Pat. No. 5,337,732 to Grundfest et al.
US Patent Application Publication 2003/0168068 to Poole and Young
US Patent Application Publication 2003/0105386 and
U.S. Pat. No. 6,485,409 to Voloshin et al. US Patent Application Publication 2002/0107478 to Wendlandt
U.S. Pat. No. 6,702,735 to Kelly
U.S. Pat. No. 5,259,364 to Bob, et al.
U.S. Pat. No. 4,403,985 to Boretos
U.S. Pat. No. 4,176,662 to Frazer
U.S. Pat. No. 4,148,307 to Utsugi
U.S. Pat. No. 5,906,591 to Dario et al.
U.S. Pat. No. 6,007,482 to Madni et al.
U.S. Pat. No. 5,662,587 to Grundfest et al.
U.S. Pat. No. 4,690,131 to Lyddy, Jr. et al.
U.S. Pat. No. 4,040,413 to Ohshiro
U.S. Pat. No. 6,503,192 to Ouchi
U.S. Pat. No. 6,814,728 to Ouchi
U.S. Pat. No. 6,911,005 to Ouchi et al.
US Patent Application Publication 2003/0083547 to Hamilton et al.
PCT Publication WO 04/069057 to Gobel
US Patent Application Publication 2003/0000526 to Gobel
PCT Publication WO 03/045487 to Gobel
U.S. Pat. No. 4,561,427 to Takada

SUMMARY OF THE INVENTION

In some embodiments of the present invention, an imaging system propelled by fluid pressure is provided for examining a gastrointestinal tract, and more specifically, a small intestine of a subject. The system comprises a guide member configured to be mounted, typically by inflation thereof, in a vicinity of an ileocecal valve or a pyloric valve of the subject, so as to form a pressure seal with the valve. The system further comprises an introducer tube arranged for sliding movement through the guide member, and a capsule removably coupled to a distal portion of the introducer tube. The capsule comprises an inflation device and an imaging element. The inflation device is configured to form a pressure seal with a wall of the small intestine, and to be advanced distally through the small intestine in response to delivery of positive gas pressure proximal to the capsule, from a gas supply. (In this context, in the specification and in the claims, "proximal" means closer to the orifice—mouth or rectum—through which the capsule is originally placed into the gastrointestinal tract, and "distal" means further from this orifice.)

In an embodiment, the gas supply is disposed within the capsule, and comprises a gas generator configured to advance the capsule by generating positive gas pressure in the small intestine, proximal to the inflation device and distal to the guide member. The gas generator thus enables distal motion of the capsule, e.g., by generating gas by hydrolysis, or by chemical means. Alternatively or additionally, the gas supply comprises a gas storage container. For some applications, the gas supply is configured to supply gas pressure to inflate the capsule's inflation device to approximately the diameter of the small intestine. Alternatively, the capsule comprises an independent inflation device diameter regulator which supplies gas pressure to the inflation device.

For some applications, a gas supply is disposed within the capsule and is configured to supply gas pressure to the inflation device but not to propel the capsule. The gas supply for propelling the capsule is coupled to a proximal end of the introducer tube and is coupled via the introducer tube to be in fluid communication with the small intestine. In this embodiment, the gas supply, located proximal to the capsule, generates the positive pressure at a remote location, propelling the capsule distally through the small intestine. For this application, the gas supply is typically disposed outside a body of the subject.

The system is typically configured to image a substantial or entire length of the small intestine, and to transmit the image to a location outside the body of the subject, e.g., by using radiofrequency transmission.

Prior to placement of the capsule in the small intestine, the capsule typically remains coupled to the introducer tube as the tube is advanced distally toward the valve of the subject. Once the guide member has been mounted to the valve and creates a pressure seal therewith, the capsule is decoupled from the introducer tube and is advanced through the small intestine. Alternatively, the capsule is introduced through the introducer tube. Upon conclusion of the procedure, the introducer tube is withdrawn, and the capsule travels through the gastrointestinal tract and is expelled through the rectum.

For some applications, the capsule is configured to release a drug into the small intestine, or to perform any other procedure known in the art.

In some embodiments in which the guide member is mounted in a vicinity of the pyloric valve, the introducer tube comprises a gastric tube or gastroscope, which is advanced through the stomach to the pyloric valve. For some applications, the capsule is introduced through a working channel of the gastroscope or through the nasogastric tube. In one example, the esophagus and stomach are examined endoscopically, and if no pathology is seen, then the capsule is introduced through a working channel of the endoscope which has in any case been advanced into the subject's stomach. For some applications, the gastric tube or gastroscope comprises a distal deflection mechanism for navigating the distal end of the tube or endoscope to the pyloric valve. For some applications in which the capsule is advanced through the pyloric valve, a vent tube is introduced into the small intestine or colon, distal to the capsule and functions to reduce pressure distal to the capsule by passing fluid from distal to the capsule to a location outside the body of the subject. Typically, the vent tube in this instance is passed through a channel of a colonoscope that is used in any case to image the subject's colon. It is noted that when the vent tube is placed in the colon, it facilitates passage from the colon of fluid which passed naturally from the small intestine to the colon.

In embodiments in which the guide member is mounted in a vicinity of the ileocecal valve, the introducer tube comprises a colonoscope and is configured to be inserted into the rectum of the subject, and advanced through the colon and cecum to the ileocecal valve. For some applications, the capsule is introduced through a working channel of the colonoscope. For some applications in which the capsule is advanced through the ileocecal valve, a vent tube is introduced into the small intestine from the stomach, distal to the capsule, and functions to reduce pressure distal to the capsule by passing fluid from distal to the capsule to a location outside the body of the subject.

In some embodiments of the present invention, an ingestible capsule comprises the inflation device and an on-board gas supply, and is configured to image the small intestine. Typically, the gas supply comprises a gas generator. Alternatively, the gas supply comprises a gas storage container. Typically, the gas supply is configured to propel the ingestible capsule distally (i.e., aborally) through the small intestine by delivering positive gas pressure to a volume of the small intestine proximal to the capsule. For some applications, the gas supply additionally provides gas pressure to inflate the inflation device. Alternatively or additionally, the capsule comprises an independent inflation device diameter regulator configured to regulate the pressure of the inflation device such that the inflation device diameter is regulated to be approximately the diameter of the small intestine.

There is therefore provided, in accordance with an embodiment of the present invention, apparatus, including:

an introducer tube, configured to be advanced into a gastrointestinal tract of a subject;

a guide member coupled to a distal end of the introducer tube and configured to be mounted in a vicinity of a valve of the subject;

a capsule removably coupled to a distal portion of the introducer tube, and configured to be decoupled from the introducer tube and propelled through a small intestine of the subject once the guide member has been mounted in the vicinity of the valve; and a gas supply configured to propel the capsule distally through the small intestine by generating positive gas pressure proximal to the capsule.

In an embodiment, the capsule includes an inflation device configured to form a pressure seal with a wall of the small intestine.

In an embodiment, the guide member is configured to be inflated and, by inflation thereof, to be mounted within the valve and to form a pressure seal therewith.

In an embodiment, the inflation device includes an inflatable balloon, and the capsule is configured to regulate a diameter of the inflatable balloon in accordance with a local diameter of the small intestine.

In an embodiment, the gas supply is configured to deliver positive gas pressure therefrom to a volume of the small intestine proximal to the inflation device and distal to the guide member.

In an embodiment, the gas supply is coupled to a proximal end of the introducer tube.

In an embodiment, the introducer tube is configured to deliver the positive gas pressure to the small intestine proximal to the capsule, and the guide member is configured to be deflated following being mounted, and to subsequently be inflated at a site distal to where the guide member had been mounted, to an extent sufficient to form a pressure seal upon inflation at the distal site.

In an embodiment, the gas supply is configured to inflate the guide member.

In an embodiment, the introducer tube is configured to be advanced distally from a mouth of the subject, and the valve includes a pyloric valve.

In an embodiment, the introducer tube includes a gastric tube.

In an embodiment, the introducer tube includes a gastroscope.

In an embodiment, the introducer tube is configured to be advanced distally from a rectum of the subject, and the valve includes an ileocecal valve.

In an embodiment, the introducer tube includes a colonoscope.

In an embodiment, the apparatus includes an imaging element, configured to image the gastrointestinal tract.

In an embodiment, the inflation device is at least 2 cm from the imaging element.

In an embodiment, the inflation device is 3-5 cm from the imaging element.

In an embodiment, the capsule includes a transmission device configured to transmit an image to a location outside of a body of the subject.

In an embodiment, the transmission device includes a radiofrequency transmission device.

In an embodiment, the apparatus includes a vent tube.

In an embodiment, the capsule includes the vent tube, and the vent tube is configured to facilitate passage of a fluid from (a) a site distal to the inflation device to (b) a site proximal to the inflation device.

In an embodiment, the vent tube includes at least one valve coupled to the vent tube and configured to facilitate unidirectional passage of a fluid therethrough.

In an embodiment, the vent tube is configured to facilitate distal motion of the capsule through the gastrointestinal tract by reducing a pressure distal to the capsule.

In an embodiment, the vent tube is configured to be advanced from a site that is distal to the capsule to a site that is less distal to the capsule, and to facilitate passage of a fluid from (a) distal to the capsule to (b) a site outside the body of the subject.

In an embodiment, the capsule is configured to be advanced distally from a pyloric valve of the subject, and the vent tube is configured to be advanced through a colon of the subject.

In an embodiment, the vent tube is configured to be advanced through the colon and then through an ileocecal valve of the subject.

In an embodiment, the vent tube is configured to be advanced through a colonoscope.

In an embodiment, the capsule is configured to be advanced distally from an ileocecal valve of the subject, and the vent tube is configured to be advanced into a small intestine of the subject through a pyloric valve of the subject.

In an embodiment, the vent tube includes a nasogastric tube.

In an embodiment, the vent tube is configured to be advanced through a gastroscope.

In an embodiment, the capsule includes the gas supply, and the gas supply includes a gas generator.

In an embodiment, the gas supply includes a gas storage container.

In an embodiment, the apparatus includes an inflation device diameter regulator, which is configured to regulate a diameter of the inflation device in accordance with a local diameter of the small intestine.

In an embodiment, the inflation device diameter regulator includes the gas supply.

In an embodiment, the inflation device diameter regulator is configured to operate independently of the gas supply.

There is additionally provided, in accordance with an embodiment of the present invention, apparatus, including:
  an ingestible capsule including:
    an inflation device configured to generate a pressure seal with a wall of a small intestine of a subject; and
    a gas supply configured to propel the inflation device distally through the small intestine of the subject.

In an embodiment, the gas supply includes a gas generator.

In an embodiment, the gas supply includes a gas storage container.

In an embodiment, the inflation device includes an inflatable balloon and the gas supply is configured to regulate a diameter of the inflatable balloon in accordance with a local diameter of the small intestine.

In an embodiment, the gas supply is configured to deliver positive gas pressure therefrom to a volume of the small intestine proximal to the inflation device and distal to a pyloric sphincter of the subject.

In an embodiment, the ingestible capsule includes a vent tube configured to facilitate passage of a fluid from (a) a site distal to the inflation device to (b) a site proximal to the inflation device.

In an embodiment, the vent tube includes at least one valve configured to be disposed in a lumen of the vent tube and configured to facilitate unidirectional passage of the fluid therethrough.

In an embodiment, the apparatus includes an imaging element, configured to image the gastrointestinal tract.

In an embodiment, the inflation device is at least 2 cm from the imaging element.

In an embodiment, the inflation device is 3-5 cm from the imaging element.

In an embodiment, the capsule includes a transmission device configured to transmit an image to a location outside of a body of the subject.

In an embodiment, the apparatus includes an inflation device diameter regulator, which is configured to regulate a diameter of the inflation device in accordance with a local diameter of the small intestine.

In an embodiment, the inflation device diameter regulator includes the gas supply.

In an embodiment, the inflation device diameter regulator is configured to operate independently of the gas supply.

There is yet additionally provided, in accordance with an embodiment of the present invention, apparatus, including:
  an ingestible capsule; and
  a vent tube coupled to the capsule, and configured to facilitate passage of a fluid from (a) a site distal to the capsule to (b) a site proximal to the capsule.

In an embodiment, the vent tube is configured to facilitate enhanced distal motion of the capsule through a gastrointestinal tract by reducing a pressure distal to the capsule.

In an embodiment, the vent tube includes at least one valve configured to be disposed within a lumen of the vent tube and configured to facilitate unidirectional passage of the fluid therethrough.

There is still additionally provided, in accordance with an embodiment of the present invention, a method, including:

distally advancing a capsule into a gastrointestinal tract of a subject;

distally advancing an introducer tube coupled to a guide member into the gastrointestinal tract;

mounting the guide member in a vicinity of a valve of the subject;

forming a pressure seal between the valve and the guide member;

forming a pressure seal between the capsule and a wall of a small intestine of the subject; and while the capsule is not physically coupled to the introducer tube, propelling the capsule distally through the small intestine by generating positive gas pressure proximal to the capsule.

In an embodiment, mounting the guide member in the vicinity of the valve includes inflating the guide member to an extent sufficient to form a pressure seal by inflation.

In an embodiment, the method includes venting a pressure distal to the capsule, through a vent tube that is distal to the capsule, to a site outside a body of the subject.

In an embodiment, the method includes venting a pressure distal to the capsule to a site proximal to the capsule.

In an embodiment, distally advancing the capsule into the gastrointestinal tract includes advancing the capsule through the introducer tube.

In an embodiment, distally advancing the capsule into the gastrointestinal tract includes advancing the capsule through a working channel of a gastroscope.

In an embodiment, distally advancing the capsule into the gastrointestinal tract includes advancing the capsule through a working channel of a colonoscope.

In an embodiment, distally advancing the capsule into the gastrointestinal tract includes advancing the capsule through a working channel of a nasogastric tube.

In an embodiment, the method includes:

deflating the guide member, subsequently to mounting the guide member;

advancing the guide member to a site distal to the vicinity of the valve; and subsequently inflating the guide member, at the distal site, to an extent sufficient to form a pressure seal by inflation.

In an embodiment, the method includes regulating a diameter of the capsule in accordance with a local diameter of the small intestine.

In an embodiment, propelling the capsule includes increasing pressure proximal to the capsule by delivering positive gas pressure by the capsule to a volume of the small intestine proximal to the capsule and distal to the valve.

In an embodiment, distally advancing the introducer tube includes distally advancing the introducer tube from a mouth of the subject, and mounting the guide member includes mounting the guide member in a vicinity of a pyloric valve of the subject.

In an embodiment, forming the pressure seal between the capsule and the small intestine includes inflating an inflation device coupled to the capsule.

In an embodiment, inflating the inflation device includes inflating the inflation device by delivering positive gas pressure to the inflation device.

In an embodiment, delivering positive gas pressure includes generating the pressure by a chemical reaction within the capsule.

In an embodiment, distally advancing the introducer tube includes distally advancing the introducer tube from a rectum of the subject, and mounting the guide member includes mounting the guide member in a vicinity of an ileocecal valve of the subject.

In an embodiment, the method includes imaging the gastrointestinal tract during distal motion of the capsule, during the propelling of the capsule distally through the small intestine.

In an embodiment, the method includes imaging the gastrointestinal tract during proximal motion of the capsule subsequent to the propelling of the capsule distally through the small intestine.

In an embodiment, the method includes imaging the gastrointestinal tract.

In an embodiment, imaging includes imaging from a site at least 2 cm from the pressure seal between the capsule and the wall of the small intestine.

In an embodiment, imaging includes imaging from a site 3-5 cm from the pressure seal between the capsule and the wall of the small intestine.

In an embodiment, imaging the small intestine includes:

generating an image of the small intestine; and in response to the generating, transmitting the generated image to a location outside of a body of the subject.

There is also provided, in accordance with an embodiment of the present invention, a method, including:

administering an ingestible capsule to a subject;

forming a pressure seal between the capsule and a wall of a small intestine of the subject; and propelling the capsule distally through the small intestine by generating positive gas pressure proximal to the capsule.

In an embodiment, the method includes regulating a diameter of a portion of the capsule in accordance with a local diameter of the small intestine.

In an embodiment, propelling the capsule includes increasing pressure proximal to the capsule by delivering positive gas pressure by the capsule to a volume of the small intestine proximal to the capsule and distal to a pyloric valve of the subject.

In an embodiment, the method includes imaging the gastrointestinal tract.

In an embodiment, imaging includes imaging from a site at least 2 cm from the pressure seal between the capsule and the wall of the small intestine.

In an embodiment, imaging includes imaging from a site 3-5 cm from the pressure seal between the capsule and the wall of the small intestine.

In an embodiment, imaging the small intestine includes:

generating an image of the small intestine; and in response to the generating, transmitting the generated image to a location outside of a body of the subject.

In an embodiment, forming the pressure seal between the capsule and the small intestine includes inflating an inflation device coupled to the capsule.

In an embodiment, inflating the inflation device includes inflating the inflation device by delivering positive gas pressure to the inflation device.

In an embodiment, delivering positive gas pressure includes generating the pressure by a chemical reaction within the capsule.

The present invention will be more fully understood from the following detailed description of embodiments thereof, taken together with the drawings, in which:

BRIEF DESCRIPTION OF THE DRAWINGS

FIG. 2 is a schematic illustration of the imaging system of FIGS. 1A and 1B during insertion of the system into the small intestine via a colon of the subject, in accordance with an embodiment of the present invention;

FIGS. 3A and 3B are schematic illustrations of the imaging system of FIGS. 1A and 1B during insertion of the system into the small intestine via a stomach of the subject, in accordance with an embodiment of the present invention.

DETAILED DESCRIPTION OF EMBODIMENTS

Figure 1A:
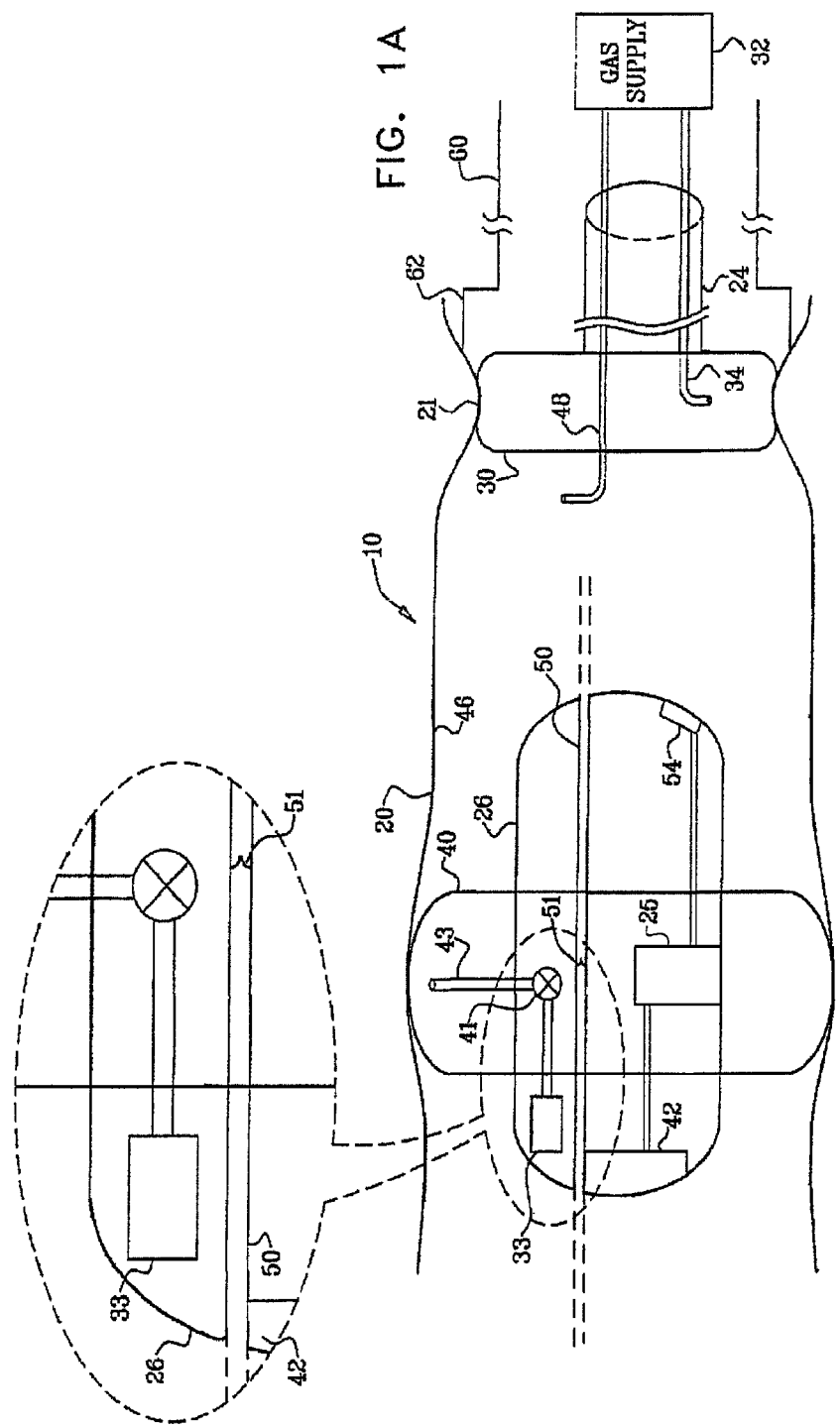
FIGS. 1A and 1B are schematic illustrations of an imaging system configured to be inserted into a small intestine of a subject via an intestinal valve, in accordance with respective embodiments of the present invention.
Figure 1B:
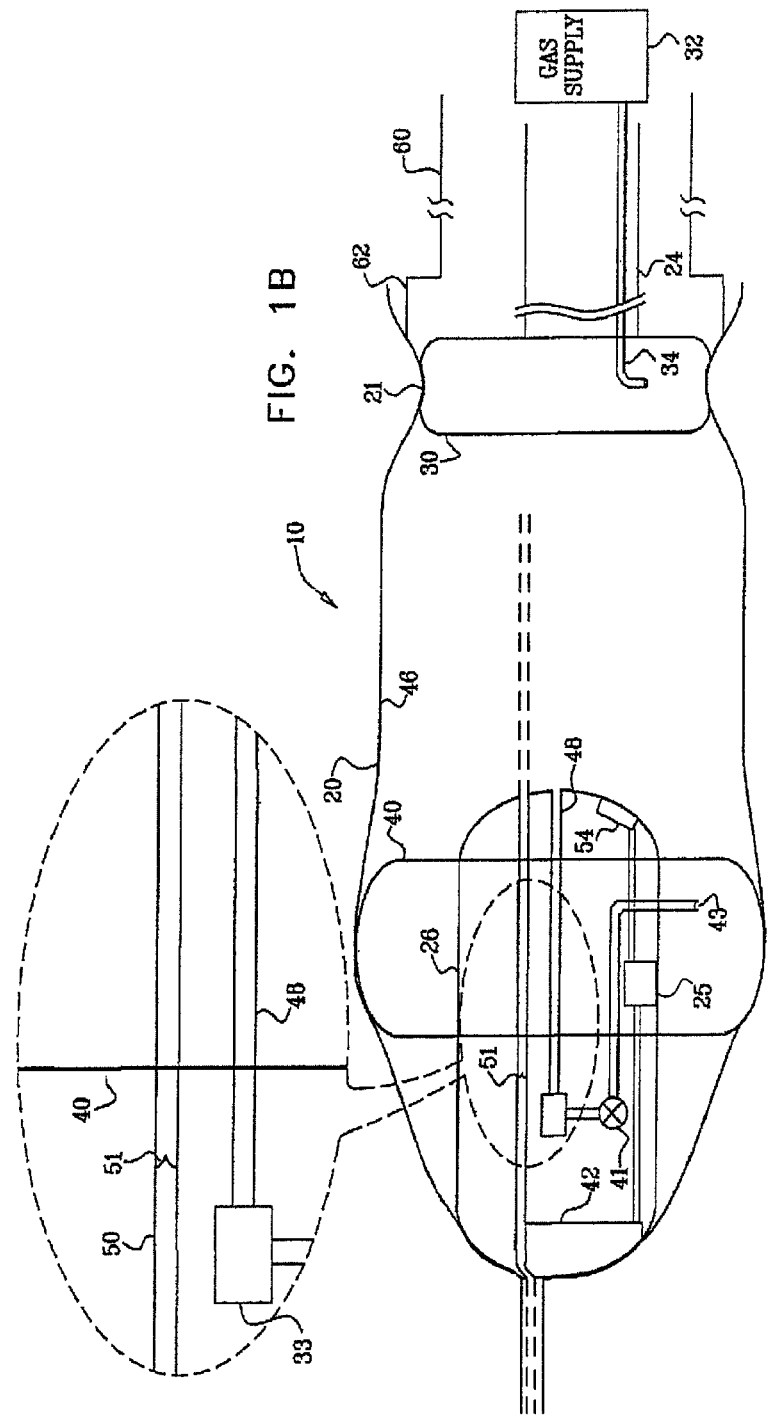

Reference is now made to FIGS. 1A and 1B, which are schematic illustrations of an imaging system 10 configured to be inserted into a small intestine 20 of a subject via an intestinal valve 21, in accordance with respective embodiments of the present invention. System 10 comprises an introducer tube 60 comprising a carrier tube 24, a capsule 26 removably coupled to a distal end of introducer tube 60, and a guide member 30. Carrier 24 typically comprises a plurality of tubes and communication wires, as described hereinbelow.

Guide member 30 is configured to be advanced distally within the gastrointestinal tract of the subject and to be mounted in a vicinity of intestinal valve 21 (either a pyloric valve or an ileocecal valve), so as to form a pressure seal with valve 21. (In this context, in the specification and in the claims, "proximal" means closer to the orifice—mouth or rectum—through which capsule 26 is originally inserted, and "distal" means further from this orifice.)

Typically, guide member 30 is inflated in order to form the pressure seal with valve 21. For some applications, guide member 30 is placed within valve 22 (as shown). For other applications, guide member 30 is placed within small intestine 20, e.g., within the duodenal bulb. For yet other applications, guide member 30 is secured adjacent to valve 21, but outside of small intestine 20.

As shown in FIGS. 1A and 1B, an interior of guide member 30 is in fluid communication with an external gas supply 32 via a guide member gas supply tube 34 which is disposed with a lumen of carrier tube 24. External gas supply 32 is coupled to a proximal end of introducer tube 60 at a location outside a body of the subject (e.g., external gas supply 32 may be configured to be mounted to a wall or may be configured to be portable). Typically, external gas supply 32 comprises a gas storage unit configured to provide a pressurized biologically-compatible fluid, such as but not limited to, a source of pressurized air, $CO_2$, or water. The provision of the fluid forms a pressure seal between guide member 30 and valve 21.

Capsule 26 comprises an on-board gas supply 33. Typically, on-board gas supply 33 comprises a gas generator configured to provide a pressurized biologically-compatible gas, such as but not limited to, a source of $CO_2$, hydrogen, or oxygen. The gas generator typically generates gas using techniques known in the art, such as electrolysis or by a chemical reaction. Alternatively or additionally, on-board gas supply 33 comprises a gas storage unit typically comprising a highly-compressed gas.

Capsule 26 comprises an inflation device 40 and, typically, an imaging element 42. Inflation device 40 is configured to be inflated in response to pressure from the capsule's on-board gas supply 33. In an embodiment, positive gas pressure is delivered to inflation device 40 from on-board gas supply 33 via an inflation device gas supply tube 43 coupled to an inflation device diameter regulator 41. Inflation device diameter regulator 41 typically comprises a valve configured to actively or passively regulate a level of gas pressure delivered to inflation device 40. Thus, the diameter of inflation device 40 is typically regulated in accordance with a local diameter of small intestine 20 and/or in accordance with a level of motion of the capsule through the gastrointestinal tract. For some applications, on-board gas supply 33 insufflates inflation device 40 by generating pressure as a by-product of a chemical reaction.

Once inflated, inflation device 40 forms a pressure seal with a wall 46 of small intestine 20. Inflation device 40, which typically but not necessarily comprises a balloon, comprises a medically-safe elastomeric material, such as polyurethane or silicone rubber.

For some applications, inflation device 40 is disposed near the center of capsule 26 (as shown in FIG. 1A). Alternatively or additionally, the center of inflation device 40 is at least 2 cm (e.g., about 3-5 cm) from the most distal portion of capsule 26 and/or at least about 2 cm (e.g., about 3-5 cm) from imaging element 42 (as shown in FIG. 1B). Typically, positioning such as is shown in FIG. 1B is such that distal motion of capsule 26 naturally causes cleaning of imaging element 42 as it slides through small intestine 20 and rubs against a wall of small intestine 20. Alternatively or additionally, other techniques for cleaning imaging element 42 known in the art are utilized.

For some applications, capsule 26 comprises a vent tube 50 in fluid communication with an area of small intestine 20 distal to inflation device 40. Vent tube 50 facilitates passage of fluid (gas and/or liquid) from (a) the area distal to inflation device 40 to (b) the area proximal to inflation device 40. Typically, vent tube 50 runs the length of capsule 26 and comprises at least one valve 51 which enables unidirectional passage of fluid from a distal area to an area proximal to inflation device 40. Vent tube 50 is configured to passively permit the passage of the fluid out of the area, or is coupled to a suction source (not shown) at the proximal end of capsule 26 for actively facilitating the passage of the fluid out of the area. Vent tube 50 is configured to facilitate distal motion of the capsule through the gastrointestinal tract by modulating the pressure distal to capsule 26. If pressure builds up distal to capsule 26, the passing of fluid to proximal to capsule 26 through vent tube 50 equalizes pressure levels on either side of capsule 26.

Imaging element 42 comprises a camera (e.g., CCD or CMOS), or an x-ray, ultrasonic, MRI, infrared, and/or microwave imaging device. For some applications, imaging element 42 comprises one or more lens configured to enable forward and omnidirectional viewing, and/or means for illuminating the small intestine. For example, techniques may be used that are described in International Patent Application PCT/IL2005/000500, filed May 11, 2005, which is assigned to the assignee of the present application and is incorporated herein by reference. Alternatively or additionally, capsule 26 comprises a rear-viewing imaging element 54. For some applications, capsule 26 comprises a sensor (e.g., a chemical, physical, pressure or pH sensor), which senses a parameter of the local environment of capsule 26 and generates data indicative of the parameter. The images generated by imaging element 42 and 54 and/or data generated by the sensor are typically transmitted to a location outside of the body of the subject, typically by radio frequency transmission. For this purpose, capsule 26 comprises a transmitter 25. Alternatively, the images and/or data are stored in capsule 26 and retrieved after capsule 26 has passed naturally from the subject.

Capsule 26 comprises a power supply, e.g., a battery, which supplies power to electronic elements described herein, e.g., imaging elements 42 and 54. For some applications, capsule 26 is configured to release a drug into small intestine 20 or to facilitate a medical procedure.

As shown in FIG. 1A, external gas supply 32 is coupled to a proximal end of introducer tube 60 and is configured to propel capsule 26 distally within small intestine 20. In this embodiment, pressure from external gas supply 32 coupled to the proximal end of introducer tube 60 is delivered via advancement gas supply tube 48 to a volume of small intestine 20 proximal to capsule 26 and distal to guide member 30. Responsively, capsule 26 is advanced through small intestine 20.

For some applications, guide member 30 remains coupled to valve 21, and a sufficient amount of pressure is delivered to small intestine 20 by external gas supply 32 in order to maintain propulsion of capsule 26 within small intestine 20. Alternatively, subsequent to inflation and mounting of guide member 30 within valve 21 and partial advancement of capsule 26 through the small intestine, guide member 30 is deflated and advanced distally into small intestine 20, a portion of the distance towards capsule 26. Guide member 30 is subsequently inflated, positive pressure is again delivered proximal to capsule 26 and distal to guide member 30, and capsule 26 is again advanced. This alternating mode of advancement is repeated until capsule 26 arrives at the end of small intestine 20.

In the embodiment in which capsule 26 is introduced into small intestine 20 through the rectum of the subject, the end of small intestine 20 includes a location in a direction of pyloric valve 22. Typically, in this embodiment, capsule 26 images small intestine 20 during distal motion toward the pyloric valve. Alternatively or additionally, subsequent to propelling capsule 26 distally toward pyloric valve 22, capsule 26 undergoes naturally-induced proximal motion (i.e., toward the rectum), and images small intestine 26 during proximal motion of capsule 26.

As shown in FIG. 1B, capsule 26 is configured to propel itself through the small intestine by on-board gas supply 33. Inflation device 40 is configured to be advanced distally through small intestine 20 in response to pressure from on-board gas supply 33 delivered, via an advancement gas supply tube 48, to a volume of small intestine 40 proximal to inflation device 40 and distal to guide member 30. On-board gas supply 33 is also typically configured to supply gas to inflation device 40 via inflation device gas supply tube 43. As described hereinabove with reference to FIG. 1A, inflation device diameter regulator 41 regulates the diameter of inflation device 40, typically in accordance with the local diameter of small intestine 20. Capsule 26 comprises a vent tube 50 and valve 51, as described hereinabove with reference to FIG. 1A. In this embodiment, external gas supply 32 coupled to the proximal end of introducer tube 60 supplies positive gas pressure to guide member 30 via guide member gas supply tube 34, and does not actively contribute to propelling of capsule 26. In an embodiment, both the external and the on-board gas supplies propel the capsule through the small intestine (configuration not shown).

Reference is made to FIG. 2, which is a schematic illustration of system 10 advanced through a colon 100 of the subject to small intestine 20, in accordance with an embodiment of the present invention. In this embodiment, introducer tube 60 (typically but not necessarily comprising a colonoscope) is used to advance capsule 26 and guide member 30 through rectum 106, colon 100 and into a cecum 104 of the subject, to ileocecal valve 122. For some applications, introducer tube 60 comprises a conventional endoscope. Alternatively, introducer tube 60 utilizes techniques for advancing through colon 100 described in one or more of the above-mentioned patent application publications to Gross, Gross et al., Goldwasser, and Cabiri et al., and/or in one or more of the patent applications mentioned hereinbelow, mutatis mutandis. For some applications, imaging element 42 is used to observe and facilitate the advancement of the capsule through the colon and/or cecum.

In some embodiments, capsule 26 is introduced into small intestine 20 through a working channel of the colonoscope following a standard examination of the colon. Such an introduction may be pre-planned, or it may be a result of not finding a particular pathology and a corresponding real-time physician determination to then examine the small intestine.

After guide member 30 has been mounted in the vicinity of ileocecal valve 122 (typically within the ileum, e.g., in the terminal ileum), guide member 30 is inflated to form a pressure seal therewith. Typically, capsule 26 is coupled to introducer tube 60 by a simple mechanical coupling mechanism, e.g., a releasable hook. Subsequent to the mounting, capsule 26 is decoupled from introducer tube 60. In an embodiment, decoupling of capsule 26 from introducer tube 60 is obtained by applying a current that heats a plastic or other fusing material linking introducer tube 60 to capsule 26, until the fusing material breaks. Alternatively, capsule 26 and introducer tube 60 are held together by a magnetic force, and an electromagnetic pulse is applied to separate capsule 26 from introducer tube 60. Further alternatively, capsule 26 and introducer tube 60 are held together by suction, and the suction is removed in order to separate capsule 26 from introducer tube 60.

Introducer tube 60 typically remains in colon 100 throughout the procedure. In such an embodiment, external gas supply 32 delivers positive gas pressure to the volume of small intestine 20 proximal to capsule 26, as described hereinabove with reference to FIG. 1A. While capsule 26 is not physically coupled to introducer tube 60, it is advanced through small intestine 20, as described hereinabove with reference to either of FIG. 1A or 1B. Capsule 26 typically forms a pressure seal with wall 46 of small intestine 20 by inflating inflation device 40. Capsule 26 then advances distally, in a direction of pyloric valve 22.

In an embodiment, guide member 30 is not utilized in the embodiment shown in FIG. 2, and introducer tube 60 is withdrawn after placing capsule 26 into small intestine 20. In this embodiment, capsule 26 generates gas pressure proximal thereto in the small intestine, and the closure of valve 122 (or portions of the small intestine proximal to the capsule) facilitate the buildup of pressure which supports distal motion of the capsule.

Figure 3B:
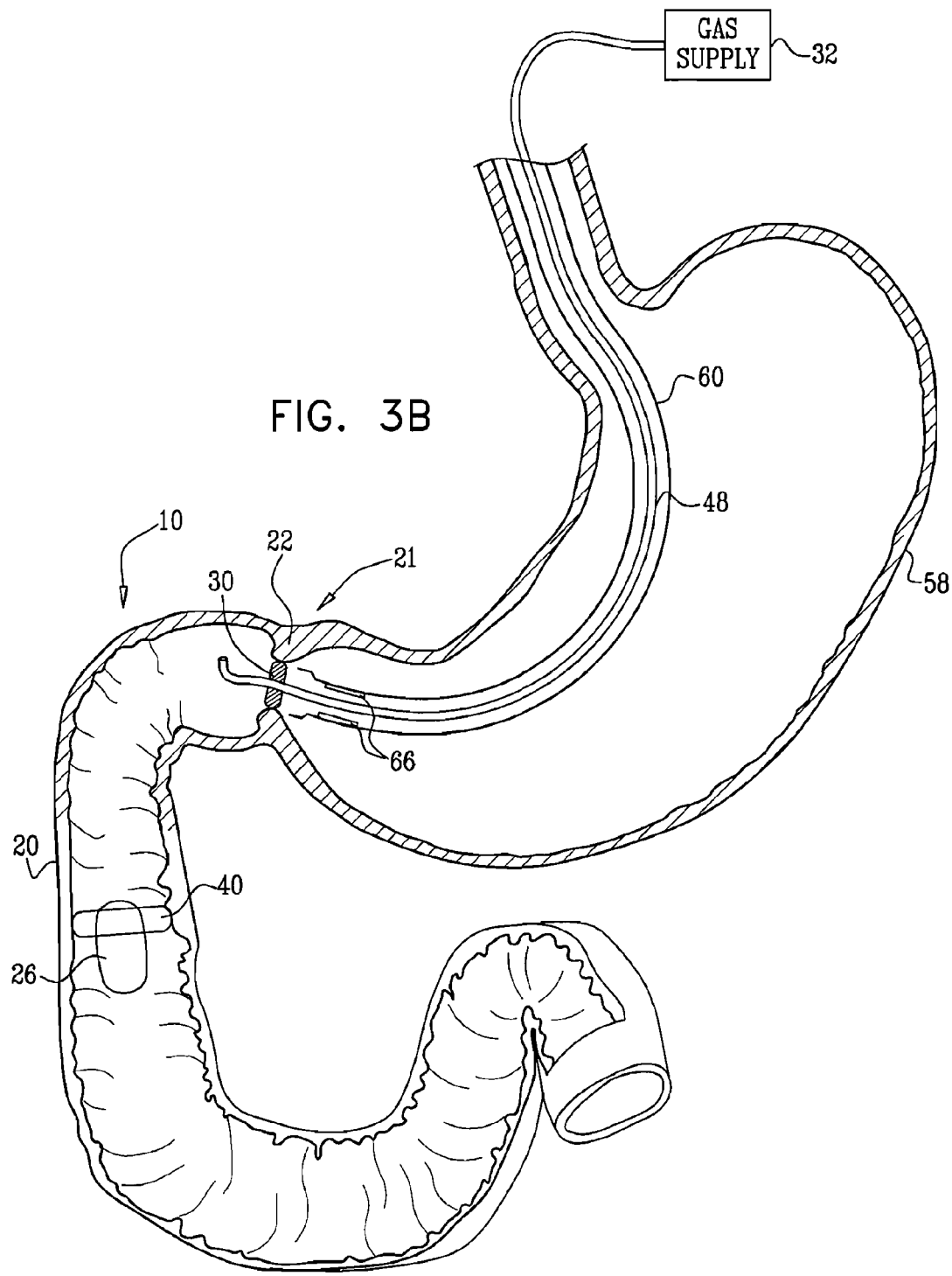

Reference is now made to FIGS. 3A and 3B, which are schematic illustrations of imaging system 10 during insertion of the system into small intestine 20 via a stomach 58 of the subject, in accordance with an embodiment of the present invention. As shown in FIG. 3A, an introducer tube 60 is used to advance capsule 26 and guide member 30 through stomach 58 of the subject to pyloric valve 22. Introducer tube 60 typically comprises a conventional gastric tube or gastroscope.

For some applications, introducer tube 60 comprises a steering mechanism 66 for deflecting a distal end of the introducer tube, such as is known in the endoscopic and catheter art. For example, steering mechanism 66 may comprise two or more guidewires configured to enable deflection of the distal end of the introducer tube in two or more directions (configuration not shown). For some applications, images generated by imaging element 42 are transmitted to a location outside the body of the subject and are used to assist in guiding capsule 26 through stomach 58 to pyloric valve 22.

For some applications, capsule 26 and guide member 30 are configured to be coupled to a distal end of introducer tube 60 by a coupling element 62, e.g., a simple mechanical coupling element such as a releasable hook. Alternatively, introducer tube 60 is advanced into stomach 58, and capsule 26 and guide member 30 are advanced through introducer tube 60, such as by pushing on carrier tube 24 (configuration not shown).

As shown in FIG. 3B, after guide member 30 has been mounted in the vicinity of pyloric valve 22, guide member 30 is inflated by external gas supply 32, and capsule 26 is decoupled from introducer tube 60. Typically, decoupling of capsule 26 from introducer tube 60 is achieved by releasing the hook. In an embodiment, decoupling of capsule 26 from introducer tube 60 is obtained by applying a current that heats a plastic or other fusing material linking introducer tube 60 to capsule 26, until the fusing material breaks. Alternatively, capsule 26 and introducer tube 60 are held together by a magnetic force, and an electromagnetic pulse is applied to separate capsule 26 from introducer tube 60. Further alternatively, capsule 26 and introducer tube 60 are held together by suction, and the suction is removed in order to separate capsule 26 from introducer tube 60.

In some embodiments, introducer tube 60 comprises an endoscope, e.g., a gastroscope, and capsule 26 is introduced into small intestine 20 through a working channel of the endoscope following a standard examination of the stomach.

Typically, guide member 30 remains coupled to introducer tube 60 after inflation of the guide member, and introducer tube 60 remains in stomach 58 throughout the procedure. While capsule 26 is not physically coupled to introducer tube 60, it is advanced through small intestine 20, as described hereinabove with reference to either of FIG. 1A or 1B.

As shown in FIGS. 3A and 3B, external gas supply 32 is disposed outside of a body of the subject (e.g., gas supply is configured to be mounted to a wall or is configured to be portable), and is configured to generate positive gas pressure to be delivered through guide member gas supply tube 34 (not shown). Additionally, external gas supply 32 generates positive gas pressure which is delivered from a remote location with respect to capsule 26 through advancement gas supply tube 48 to a volume of small intestine 20 proximal to capsule 26 and distal to guide member 30, so as to propel capsule 26 distally through small intestine.

System 10 is typically configured to image an entire length of small intestine 20. Imaging element 42 typically transmits images in real time to an external monitor for viewing by the operator of the system who is performing the procedure. Typically, the imaging element wirelessly transmits, e.g., using radiofrequency transmission, the images to the external monitor.

In an embodiment, capsule 26 comprises one or more electrodes configured to stimulate contractile tissue of wall 46 of small intestine 20, so as to propel capsule 26 proximally towards pyloric valve 22. Techniques for such stimulation may be used that are described in the above-mentioned U.S. Pat. No. 6,709,388 to Mosse et al. For some applications, such electrical stimulation techniques are used alternatively or additionally to advance and/or hold the capsule in place in small intestine 20. Capsule 26 may be designed for single use or, alternatively, for multiple uses.

Upon conclusion of the procedure, capsule 26 typically travels through the gastrointestinal tract and is excreted through the rectum.

Reference is now made to FIGS. 1A-3B. For some applications, a vent tube is advanced into the gastrointestinal tract of the subject, prior to or during the distal advancing of capsule 26 through small intestine 20. Typically, the vent tube is introduced into a valve distal to the valve through which capsule 26 was originally introduced, or to a site distal to that distal valve. The vent tube functions to reduce pressure distal to capsule 26 by facilitating passage of fluid from (a) a site distal to the capsule 26 to (b) a site outside the body of the subject. For applications in which capsule 26 advances distally from pyloric valve 22, the vent tube is advanced into the colon or small intestine via a tube, e.g., a colonoscope.

For applications in which capsule 26 advances distally from ileocecal valve 122, the vent tube is advanced through pyloric valve 22 via a tube, e.g., a gastroscope or a nasogastric tube. Alternatively, the vent tube comprises a nasogastric tube and is advanced into the stomach and through the pyloric valve of the subject. Use of a vent tube placed at a distal valve, as described, may be practiced in combination with or separately from a vent tube 50 in capsule 26, as shown in FIGS. 1A-B.

Figure 4A:
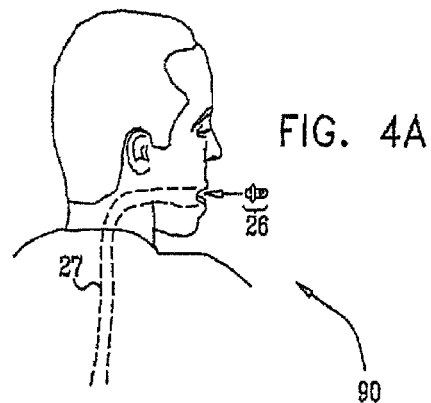
FIGS. 4A and 4B are schematic illustrations of an ingestible capsule imaging system, in accordance with an embodiment of the present invention.
Figure 4B:
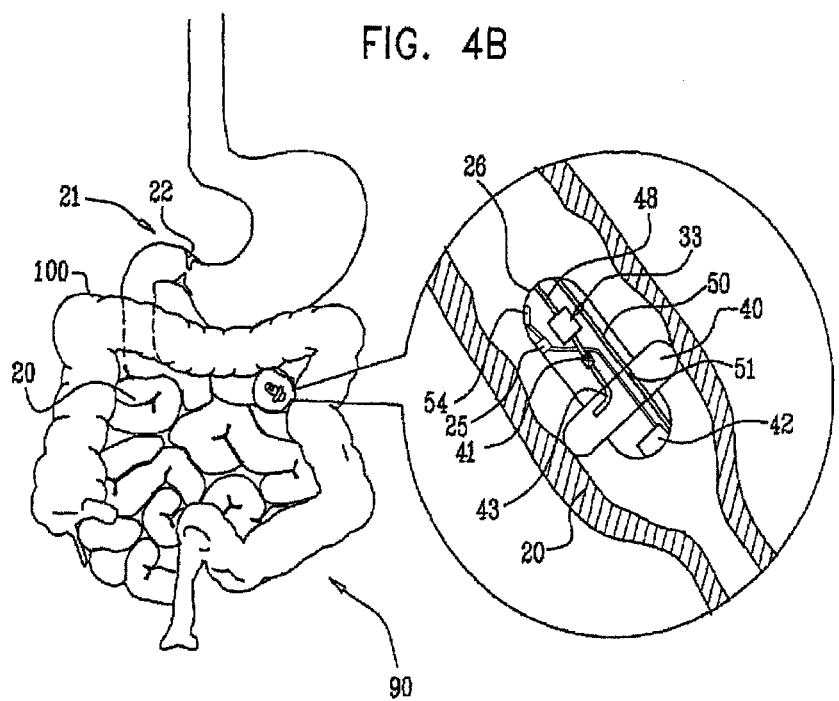

Reference is now made to FIGS. 4A and 4B, which are schematic illustrations of an ingestible capsule imaging system 90, in accordance with an embodiment of the present invention. Capsule 26 comprises inflation device 40 and on-board gas supply 33, as described hereinabove with reference to FIG. 1B. In this embodiment, the subject swallows capsule 26 (FIG. 4A), capsule 26 travels down esophagus 27 by natural peristalsis, and imaging of small intestine 20 is achieved without the use of introducer tube 60 and guide member 30.

In an embodiment, capsule 26 comprises a memory storage unit which stores the acquired images generated by imaging elements 42 and 54. Images are analyzed subsequent to passing and retrieval of capsule 26 from the subject.

Alternatively, capsule 26 comprises a data transmitter 25 configured to transmit images to an external storage device using radiofrequency transmission. For some applications, external storage device comprises an article configured to be worn by the subject during the examination procedure by capsule 26 while the subject is free to walk ad libitum. Images are stored by the external storage device, and are analyzed by a physician following the examination procedure. Typically, active propulsion of capsule 26, as provided by the embodiments of FIGS. 4A-B, allows an examination procedure to last substantially shorter than if the capsule were not propelled.

Although inflation device 40 has been described in embodiments of the present invention as being in direct contact with wall 46 of small intestine 20, the scope of the invention includes establishing contact between the inflation device and the wall of the intestine through an intermediary, such as a sheath surrounding the inflation device.

The scope of the present invention includes embodiments described in the following applications, all of which are assigned to the assignee of the present application and are incorporated herein by reference. In an embodiment, techniques and apparatus described in one or more of the following applications are combined with techniques and apparatus described herein. In particular, such techniques may be used for advancing capsule 26 through small intestine 20 and/or through colon 100.

US Patent Application Publication 2005/0154355 to Gross et al.

US Patent Application Publication 2004/0102681 to Gross

US Patent Application Publication 2005/0036059 to Goldwasser

US Patent Application Publications 2005/0038318 and 2005/0038319 to Goldwasser

US Patent Application Publication 2005/0038335 to Gross et al.

US Patent Application Publication 2005/0154278 to Cabiri et al.

PCT Publication WO 05/065044 to Cabiri et al.

U.S. patent application Ser. No. 10/967,922 to Cabiri et al., filed Oct. 18, 2004, entitled, "Pressure-propelled system for body lumen"

U.S. patent application Ser. No. 10/523,578 to Gross et al., filed Jan. 28, 2005, entitled, "Self-propelled imaging system"

U.S. Provisional Patent Application 60/571,438 to Dotan et al., filed May 14, 2004, entitled, "Omnidirectional and forward-looking imaging device"

U.S. Provisional Patent Application 60/607,986 to Cabiri et al., filed Sep. 8, 2004, entitled, "Mechanical aspects of pressure-propelled system for body lumen"

U.S. Provisional Patent Application 60/642,245, filed Jan. 6, 2005, entitled, "Gastrointestinal tool over guidewire"

International Patent Application PCT/IL2005/000178 to Goldwasser et al., filed Feb. 10, 2005, entitled, "Gastrointestinal tool over guidewire"

U.S. Provisional Patent Application 60/652,049 to Goldwasser et al., filed Feb. 10, 2005, entitled "Advanced techniques for gastrointestinal tool with guiding element"

U.S. Provisional Patent Application 60/680,074 to Degtiar et al., filed May 11, 2005, entitled, "Disposable endoscope connector"

PCT Publication WO 05/110186 to Dotan et al., filed May 11, 2005, entitled, "Omnidirectional and forward-looking imaging device"

U.S. patent application Ser. No. 10/753,424 to Gross et al., entitled, "Pressure-propelled system for body lumen," filed Jan. 9, 2004

U.S. Provisional Patent Application 60/704,656 to Goldwasser et al., entitled, "Tools for use in esophagus," filed Aug. 1, 2005

PCT Publication WO 06/120689 to Degtiar et al., entitled, "Disposable endoscope connector," filed May 11, 2006

PCT Publication WO 06/120690 to Cabiri et al., entitled, "Endoscopic measurement techniques," filed May 11, 2006

PCT Patent Application PCT/IL2006/000889 to Goldwasser et al., entitled, "Tools for use in small intestine," filed Aug. 1, 2006

PCT Patent Application PCT/IL2006/000890 to Goldwasser et al., entitled, "Tools for use in esophagus," filed Aug. 1, 2006 a US provisional patent application, entitled, "Diagnostic or treatment tool for colonoscopy," filed on Jan. 17, 2007, by Cabiri et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    an introducer tube, configured to be advanced into a gastrointestinal tract of a subject;
    a guide member coupled to a distal end of the introducer tube said guide member being configured to be inflated and, by inflation thereof, to be mounted within a valve of the subject and to form a pressure seal therewith;
    a capsule removably coupled to a distal portion of the introducer tube, said capsule comprising an inflation device configured to form a pressure seal with a wall of the small intestine;
    a gas supply configured to propel the capsule distally through the small intestine by generating positive gas pressure proximal to the capsule, such that when said capsule is decoupled from the introducer tube; said capsule is propelled through a small intestine of the subject; and
    a vent tube configured to be advanced from a site that is distal to the capsule to a site that is less distal in the capsule, and to facilitate passage of a fluid from a site distal to the capsule to a site outside the body of the subject;
    the capsule being configured to be advanced distally from a pyloric valve of the subject,
    and wherein the vent tube is configured to be advanced through a colon of the subject.

2. The apparatus according to claim 1, wherein the inflation device comprises an inflatable balloon, and wherein the capsule is configured to regulate a diameter of the inflatable balloon in accordance with a local diameter of the small intestine.

3. The apparatus according to claim 1, wherein the gas supply is configured to deliver positive gas pressure therefrom to a volume of the small intestine proximal to the inflation device and distal to the guide member.

4. The apparatus according to claim 1, wherein the gas supply is coupled to a proximal end of the introducer tube.

5. The apparatus according to claim 4, wherein the introducer tube is configured to deliver the positive gas pressure to the small intestine proximal to the capsule, and wherein the guide member is configured to be deflated following being mounted, and to subsequently be inflated at a site distal to where the guide member had been mounted, to an extent sufficient to form a pressure seal upon inflation at the distal site.

6. The apparatus according to claim 1, wherein the gas supply is configured to inflate the guide member.

7. The apparatus according to claim 1, wherein the introducer tube is configured to be advanced distally from a rectum of the subject, and wherein the valve includes an ileocecal valve.

8. The apparatus according to claim 7, wherein the introducer tube comprises a colonoscope.

9. The apparatus according to claim 1, wherein said capsule comprises an imaging element, configured to image the gastrointestinal tract.

10. The apparatus according to claim 9, wherein the inflation device is at least 2 cm from the imaging element.

11. The apparatus according to claim 9, wherein the inflation device is 3-5 cm from the imaging element.

12. The apparatus according to claim 9, wherein the capsule comprises a transmitter configured to transmit an image to a location outside of a body of the subject.

13. The apparatus according to claim 12, wherein the transmitter comprises a radiofrequency transmission device.

14. The apparatus according to claim 1, wherein the capsule comprises the vent tube, and wherein the vent tube is configured to facilitate passage of a fluid from a site distal to the inflation device to a site proximal to the inflation device.

15. The apparatus according to claim 1, wherein the vent tube comprises at least one valve coupled to the vent tube and configured to facilitate unidirectional passage of a fluid therethrough.

16. The apparatus according to claim 1, wherein the vent tube is configured to facilitate distal motion of the capsule through the gastrointestinal tract by reducing a pressure distal to the capsule.

17. The apparatus according to claim 1, wherein the vent tube is configured to be advanced through the colon and then through an ileocecal valve of the subject.

18. The apparatus according to claim 1, wherein the vent tube is configured to be advanced through a colonoscope.

19. The apparatus according to claim 1, wherein the capsule comprises the gas supply, and wherein the gas supply comprises a gas generator.

20. The apparatus according to claim 19, wherein the as supply comprises a gas storage container.

21. The apparatus according to claim 1, comprising an inflation device diameter regulator, which is configured to regulate a diameter of the inflation device in accordance with a local diameter of the small intestine.

22. The apparatus according to claim 21, wherein the inflation device diameter regulator comprises the gas supply.

23. The apparatus according to claim 21, wherein the inflation device diameter regulator is configured to operate independently of the gas supply.

24. Apparatus, comprising:
an introducer tube, configured to be advanced into a gastrointestinal tract of a subject;
a guide member coupled to a distal end of the introducer tube said guide member being configured to be inflated and, by inflation thereof, to be mounted within a valve of the subject and to form a pressure seal therewith;
a capsule removably coupled to a distal portion of the introducer tube, said capsule comprising an inflation device configured to form a pressure seal with a wall of the small intestine;
a gas supply configured to propel the capsule distally through the small intestine by generating positive gas pressure proximal to the capsule, such that when said capsule is decoupled from the introducer tube; said capsule is propelled through a small intestine of the subject; and;
a vent tube configured to be advanced from a site that is distal to the capsule to a site that is less distal to the capsule, and to facilitate passage of a fluid from a site distal to the capsule to a site outside the body of the subject;
the capsule being configured to be advanced distally from an ileocecal valve of the subject, and wherein the vent tube is configured to be advanced into a small intestine of the subject through a pyloric valve of the subject.

25. The apparatus according to claim 24, wherein the inflation device comprises an inflatable balloon, and wherein the capsule is configured to regulate a diameter of the inflatable balloon in accordance with a local diameter of the small intestine.

26. The apparatus according to claim 24, wherein the gas supply is configured to deliver positive gas pressure therefrom to a volume of the small intestine proximal to the inflation device and distal to the guide member.

27. The apparatus according to claim 24, wherein the gas supply is coupled to a proximal end of the introducer tube.

28. The apparatus according to claim 27, wherein the introducer tube is configured to deliver the positive gas pressure to the small intestine proximal to the capsule, and wherein the guide member is configured to be deflated following being mounted, and to subsequently be inflated at a site distal to where the guide member had been mounted, to an extent sufficient to form a pressure seal upon inflation at the distal site.

29. The apparatus according to claim 24, wherein the gas supply is configured to inflate the guide member.

30. The apparatus according to claim 24, wherein the introducer tube is configured to be advanced distally from a rectum of the subject, and wherein the valve includes an ileocecal valve.

31. The apparatus according to claim 30, wherein the introducer tube comprises a colonoscope.

32. The apparatus according to claim 24, wherein said capsule comprising an imaging element, configured to image the gastrointestinal tract.

33. The apparatus according to claim 32, wherein the inflation device is at least 2 cm from the imaging element.

34. The apparatus according to claim 32, wherein the inflation device is 3-5 cm from the imaging element.

35. The apparatus according to claim 32, wherein the capsule comprises a transmitter configured to transmit an image to a location outside of a body of the subject.

36. The apparatus according to claim 35, wherein the transmitter comprises a radiofrequency transmission device.

37. The apparatus according to claim 24, wherein the capsule comprises the vent tube, and wherein the vent tube is configured to facilitate passage of a fluid from a site distal to the inflation device to a site proximal to the inflation device.

38. The apparatus according to claim 24, wherein the vent tube comprises at least one valve coupled to the vent tube and configured to facilitate unidirectional passage of a fluid therethrough.

39. The apparatus according to claim 24, wherein the vent tube is configured to facilitate distal motion of the capsule through the gastrointestinal tract by reducing a pressure distal to the capsule.

40. The apparatus according to claim 24, wherein the vent tube comprises a nasogastric tube.

41. The apparatus according to claim 24, wherein the vent tube is configured to be advanced through a gastroscope.

42. The apparatus according to claim 24, wherein the capsule comprises the gas supply, and wherein the gas supply comprises a gas generator.

43. The apparatus according to claim 42, wherein the gas supply comprises a gas storage container.

44. The apparatus according to claim 24, comprising an inflation device diameter regulator, which is configured to regulate a diameter of the inflation device in accordance with a local diameter of the small intestine.

45. The apparatus according to claim 44, wherein the inflation device diameter regulator comprises the gas supply.

46. The apparatus according to claim 44, wherein the inflation device diameter regulator is configured to operate independently of the gas supply.

* * * * *

UNITED STATES PATENT AND TRADEMARK OFFICE
CERTIFICATE OF CORRECTION

PATENT NO. : 8,430,809 B2  Page 1 of 1
APPLICATION NO. : 11/672369
DATED : April 30, 2013
INVENTOR(S) : Oz Cabiri et al.

It is certified that error appears in the above-identified patent and that said Letters Patent is hereby corrected as shown below:

On the title page item (75), line 2, "Inventors", please correct the spelling of the first name of inventor Boris Degtiar from "Borisr" to -- Boris --.

Signed and Sealed this
Eleventh Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,430,809 B2
APPLICATION NO. : 11/672369
DATED : April 30, 2013
INVENTOR(S) : Oz Cabiri et al.

It is certified that error appears in the above-identified patent and that said Letters Patent is hereby corrected as shown below:

In the Claims

In claim 20, at column 17, line number 24, please change the last word in the line, "as", to --gas--.

Signed and Sealed this
Fourteenth Day of October, 2014

Michelle K. Lee
*Deputy Director of the United States Patent and Trademark Office*